(12) United States Patent
Smith

(10) Patent No.: US 6,458,838 B1
(45) Date of Patent: Oct. 1, 2002

(54) ADRENOLEUKODYSTROPHY TREATMENTS

(75) Inventor: Kirby D. Smith, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/806,254

(22) PCT Filed: Sep. 28, 1999

(86) PCT No.: PCT/US99/22415

§ 371 (c)(1),
(2), (4) Date: Jul. 20, 2001

(87) PCT Pub. No.: WO00/18394

PCT Pub. Date: Apr. 6, 2000

Related U.S. Application Data

(60) Provisional application No. 60/102,186, filed on Sep. 28, 1999.

(51) Int. Cl.7 .................... A61K 31/225; A61K 31/195; A61K 31/21; A61K 38/00
(52) U.S. Cl. ..................... 514/547; 514/565; 514/2; 514/510
(58) Field of Search .................... 514/2, 8, 21, 510 514/547, 565

(56) References Cited

U.S. PATENT DOCUMENTS

| | | | |
|---|---|---|---|
| 5,530,010 A | | 6/1996 | Glasebrook ................. 514/317 |
| 5,852,056 A | * | 12/1998 | Samid ......................... 514/510 |
| 5,939,455 A | * | 8/1999 | Rephaeli ..................... 514/547 |
| 6,355,677 B1 | * | 3/2002 | Smith .......................... 514/510 |

OTHER PUBLICATIONS

"A mouse model for X–linked adrenoleukodystrophy", Lu et al., 1997, Proc. Natl. Acad. Sci., vol. 94, pp. 9366–9371.*

Singh, I., et al.: "Lovastain and sodium phenylacetate normalize the levels of very long chain fatty Acids in skin fibroblasts of X–adrenoleukodystrophy", FEBS Letters, vol. 426, No. 3, Apr. 24, 1998, pp. 342–346 XP000872899.

* cited by examiner

*Primary Examiner*—Zohreh Fay
*Assistant Examiner*—Brian-Yong S. Kwon
(74) *Attorney, Agent, or Firm*—Banner & Witcoff, Ltd.

(57) ABSTRACT

4-phenylbutyrate treatment of cells from both X-ALD patients and X-ALD knockout mice results in decreased levels of and increased β-oxidation of very-long-chain fatty acids; increased expression of the peroxisomal protein ALDRP; and induction of peroxisome proliferation. ALDP and ALDRP are functionally related, and ALDRP cDNA can complement X-ALD fibroblasts. Dietary 4-phenylbutyrate treatment is effective, producing a substantial reduction of very-long-chain fatty acid levels in the brain and adrenal glands of X-ALD mice.

11 Claims, 7 Drawing Sheets

FIG. 1a

Mouse Primary Fibroblasts

| Gene | Normal | | X-ALD | | bp |
|---|---|---|---|---|---|
| | − | + | − | + | |
| ALD | | ■ | nd | nd | 526 |
| ALDR | | | | | 711 |
| PMP70 | | | | | 405 |
| GAPDH | | | | | 528 |

FIG. 1b

Human Primary Fibroblasts

| Gene | Normal | | X-ALD | | X-ALD | | bp |
|---|---|---|---|---|---|---|---|
| | − | + | − | + | − | + | |
| ALD | | ■ | nd | nd | nd | nd | 249 |
| ALDR | | | | | | | 312 |
| PMP70 | | | | | | | 405 |
| PMP69 | | | | | | | 319 |
| AOX | | | | | | | 405 |
| β-Actin | | | | | | | 460 |

SEQUENCE LISTING

<160> NUMBER OF SEQ ID NOS: 30

<210> SEQ ID NO 1
<211> LENGTH: 18
<212> TYPE: DNA
<213> ORGANISM: Homo sapiens

<400> SEQUENCE: 1
ggagctggtg gcagagga                                                18

<210> SEQ ID NO 2
<211> LENGTH: 18
<212> TYPE: DNA
<213> ORGANISM: Homo sapiens

<400> SEQUENCE: 2
acagccacca tgagcagg                                                18

<210> SEQ ID NO 3
<211> LENGTH: 24
<212> TYPE: DNA
<213> ORGANISM: Mus musculus

<400> SEQUENCE: 3
cctatcatca cacccactgg agag                                         24

<210> SEQ ID NO 4
<211> LENGTH: 21
<212> TYPE: DNA
<213> ORGANISM: Mus musculus

<400> SEQUENCE: 4
gcagtgcgat accagcatcm g                                            21

<210> SEQ ID NO 5
<211> LENGTH: 18
<212> TYPE: DNA
<213> ORGANISM: Homo sapiens

<400> SEQUENCE: 5
tttgaagttc gatctggg                                                18

<210> SEQ ID NO 6
<211> LENGTH: 20
<212> TYPE: DNA
<213> ORGANISM: Homo sapiens

<400> SEQUENCE: 6
atccaaaatg gcaaactggg                                              20

<210> SEQ ID NO 7
<211> LENGTH: 18
<212> TYPE: DNA
<213> ORGANISM: Mus musculus

<400> SEQUENCE: 7
ttrgaagttc gatctggg                                                18

<210> SEQ ID NO 8
<211> LENGTH: 20
<212> TYPE: DNA
<213> ORGANISM: Mus musculus

```
<400> SEQUENCE: 8
atccaaaatg gcaaactggg                                                        20

<210> SEQ ID NO 9
<211> LENGTH: 24
<212> TYPE: DNA
<213> ORGANISM: Homo sapiens

<400> SEQUENCE: 9
gctgtcagca ttgatgtcga agga                                                   24

<210> SEQ ID NO 10
<211> LENGTH: 15
<212> TYPE: DNA
<213> ORGANISM: Homo sapiens

<400> SEQUENCE: 10
ttaagatgtc tcatc                                                             15

<210> SEQ ID NO 11
<211> LENGTH: 23
<212> TYPE: DNA
<213> ORGANISM: Mus musculus

<400> SEQUENCE: 11
tggtggcttc caggctaaac ttc                                                    23

<210> SEQ ID NO 12
<211> LENGTH: 23
<212> TYPE: DNA
<213> ORGANISM: Mus musculus

<400> SEQUENCE: 12
ccgagtcttc ccccagaatt ttg                                                    23

<210> SEQ ID NO 13
<211> LENGTH: 20
<212> TYPE: DNA
<213> ORGANISM: Homo sapiens

<400> SEQUENCE: 13
ctcactgagc accttcaccg                                                        20

<210> SEQ ID NO 14
<211> LENGTH: 20
<212> TYPE: DNA
<213> ORGANISM: Homo sapiens

<400> SEQUENCE: 14
ctccctccag cttctcctga                                                        20

<210> SEQ ID NO 15
<211> LENGTH: 20
<212> TYPE: DNA
<213> ORGANISM: Homo sapiens

<400> SEQUENCE: 15
cagccacgta tgaccctgaa                                                        20

<210> SEQ ID NO 16
<211> LENGTH: 20
<212> TYPE: DNA
```

<213> ORGANISM: Homo sapiens

<400> SEQUENCE: 16
ctcccacaag gaaggacctg                                             20

<210> SEQ ID NO 17
<211> LENGTH: 24
<212> TYPE: DNA
<213> ORGANISM: Mus musculus

<400> SEQUENCE: 17
tcacgcacgt ctrggatggt agtc                                        24

<210> SEQ ID NO 18
<211> LENGTH: 24
<212> TYPE: DNA
<213> ORGANISM: Mus musculus

<400> SEQUENCE: 18
ccaacaggtt ccacaaaatt gacc                                        24

<210> SEQ ID NO 19
<211> LENGTH: 24
<212> TYPE: DNA
<213> ORGANISM: Homo sapiens

<400> SEQUENCE: 19
agagcccgtr atctgaagag trcc                                        24

<210> SEQ ID NO 20
<211> LENGTH: 23
<212> TYPE: DNA
<213> ORGANISM: Homo sapiens

<400> SEQUENCE: 20
caccagcttg agtcgaatcg ttc                                         23

<210> SEQ ID NO 21
<211> LENGTH: 23
<212> TYPE: DNA
<213> ORGANISM: Mus musculus

<400> SEQUENCE: 21
gattrctcag tccatcggtg agg                                         23

<210> SEQ ID NO 22
<211> LENGTH: 23
<212> TYPE: DNA
<213> ORGANISM: Mus musculus

<400> SEQUENCE: 22 gaagcccta cagccttcac atg                                          23

<210> SEQ ID NO 23
<211> LENGTH: 31
<212> TYPE: DNA
<213> ORGANISM: Homo sapiens

<400> SEQUENCE: 23
cccgtcgacg gacgccttca cccgcttcac c                           31

<210> SEQ ID NO 24
<211> LENGTH: 38
<212> TYPE: DNA
<213> ORGANISM: Homo sapiens

<400> SEQUENCE: 24
ccacgcggcc gctcacagct ggtccaaagg ggttcagg                    38

<210> SEQ ID NO 25
<211> LENGTH: 33
<212> TYPE: DNA
<213> ORGANISM: Mus musculus

<400> SEQUENCE: 25
cccggtacca tggacgcctr catccgagtc gcc                         33

<210> SEQ ID NO 26
<211> LENGTH: 33
<212> TYPE: DNA
<213> ORGANISM: Mus musculus

<400> SEQUENCE: 26
cccggatccg cgggccttca gtttcagctg agg                         33

<210> SEQ ID NO 27
<211> LENGTH: 22
<212> TYPE: DNA
<213> ORGANISM: Homo sapiens

<400> SEQUENCE: 27
tttgagacct tcaacacccc ag                                     22

<210> SEQ ID NO 28
<211> LENGTH: 19
<212> TYPE: DNA
<213> ORGANISM: Homo sapiens

<400> SEQUENCE: 28
tttcgtggat gccacagga                                         19

<210> SEQ ID NO 29
<211> LENGTH: 20
<212> TYPE: DNA
<213> ORGANISM: Homo sapiens

<400> SEQUENCE: 29
accaccatgg agaaggctgg                                        20

<210> SEQ ID NO 30
<211> LENGTH: 20
<212> TYPE: DNA
<213> ORGANISM: Homo sapiens

```
<400> SEQUENCE: 30
ctcagtgtag cccaggatgc                                                    20
```

ADRENOLEUKODYSTROPHY TREATMENTS

This is a U.S. National Phase Application Under 35 USC 371, which was published under PCT Article 21(2) in English, and claims the benefit of U.S. Provisional Application Serial No. 60/102,186 filed Sep. 28, 1999.

This invention was made using funds from the U.S. government. Under the terms of NIH grants HD 1 098 1, HD2406 1, DK51149, and GM07814, the U.S. government may retain certain rights in the invention.

TECHNICAL FIELD OF THE INVENTION

This invention is related to adrenoleukodystrophy. In particular, it is related to identification of mechanisms for overcoming the biochemical defects of this disease.

BACKGROUND OF THE INVENTION

Functional gene redundancy and/or redundant metabolic pathways may be a fundamental aspect of vertebrate evolution. The observation that null mutations in mouse models of human disease created by targeted gene disruption often have no relevant clinical phenotype or a more subtle one than predicted has been explained in part by genetic redundancy. Redundant genes that can completely or partially substitute for each other are candidates for an approach to gene therapy for genetic disease that is based on increased expression of an endogenous gene rather than the introduction of a normal copy of the defective gene by transgenesis. This approach avoids the complications inherent in transgene gene therapy, such as targeting expression to the appropriate tissue and the immunosurveillance of tissues expressing the new transgene. In principle, enhanced gene expression could be accomplished in utero, allowing for early intervention. Initial exploration of pharmacologic induction of redundant genes in a clinical setting involved the stimulation of fetal hemoglobin by 5-azacytidine, hydroxyurea, sodium butyrate and sodium 4-phenylbutyrate to ameliorate the effects of adult hemoglobinopathies. Such an approach might be useful in Duchenne muscular dystrophy by increasing the expression of utrophin, a protein that is structurally similar to dystrophin, the abnormal protein in this genetic disorder. As more functional gene redundancy is recognized, increased expression of a related gene could become a general approach to the treatment of genetic disease. X-linked adrenoleukodystrophy (X-ALD; Mendelian Inheritance in Man number 300100) is a candidate for such pharmacological gene therapy.

X-ALD is associated with defective peroxisomal β-oxidation of saturated very-long-chain fatty acids (VLCFA) and reduced activity of peroxisomal VLCF-acyl CoA synthetase. It affects mainly central and peripheral myelin, the adrenal cortex and the testis[12]. X-ALD shows a highly variable clinical phenotype including a rapidly progressive childhood cerebral form (CCER), with inflammatory cerebral demyelination; a milder adult form, adrenomyeloneuropathy (AMN) that is slowly regressive and with initial symptoms limited to the spinal cord and peripheral nerves of the limbs; and a form (Addison-only) in which there is adrenal insufficiency without neurologic involvement. All forms of X-ALD segregate in the same families and arise from identical mutations-including null mutations.

The gene for X-ALD, identified by positional cloning, encodes a peroxisomal membrane protein (ALDP) with a predicted molecular mass of 83 kDa. Based on sequence homology, it belongs to the ATP-binding cassette (ABC) superfamily of transmembrane transporters, with the structure of a half-transporter. Although peroxisomal VLCF-acyl CoA synthetase activity is impaired in X-ALD, mutational analysis- and complementation studies[20,21] have shown that the gene for ALDP and not that for VLCF-acyl CoA synthetase is responsible for X-ALD.

There are three additional mammalian peroxisomal membrane ABC half-transporters that are closely related by nucleic acid and protein sequence: ALDRP (ALDPL1), an ALDP related protein; PMP70, a 70-kDa protein; and PMP69 (P70R), a 69-kDa protein. The function(s) of the peroxisomal ABC half-transporters and their interaction with VLCF-acyl CoA synthetase is unknown, but their considerable sequence similarity indicates that they might have related and/or overlapping function(s) in peroxisomal fatty acid metabolism. This is supported by the observations that X-ALD cells lacking ALDP have a residual activity for VLCFA β-oxidation, which could result from one or more of the other peroxisomal ABC half-transporters; and that PMP70 overexpression partially restores VLCFA β-oxidation in X-ALD fibroblasts, indicating that other peroxisomal ABC half-transporters can substitute, at least in part, for the absence of ALDP. In addition, the high level of identity between ALDP and ALDRP has led to speculation that these proteins might be functionally related.[23]

We have generated a mouse model for X-ALD by targeted gene disruption[29]. The X-ALD mouse has elevated levels of VLCFA in tissues that resemble the characteristic biochemical defect in X-ALD patients. Thus, the in vivo efficacy of treatment can be monitored by determination of its effect on VLCFA levels in the tissues, brain and adrenal gland, the organs most affected in X-ALD.

At present, no completely satisfactory therapy for X-ALD is available. Some success has been achieved with bone marrow transplantation[30,31]. Lorenzo oil, a dietary therapy, depresses plasma and liver levels of VLCFA within a month; however, it has no effect on the clinical course of the disease, perhaps because erucic acid, the active ingredient of Lorenzo oil, does not get into the brain[12,11]. Thus, new therapy for X-ALD is needed.

4-Phenyl butyrate (4-PBA) has been used for many years in the treatment of patients with urea cycle disorders[34] with few, if any, side effects. Although details of their mode of action are unclear, 4-PBA and other butyrate derivatives seem to increase expression of certain target genes[35-38]. Fenofibrate, a compound structurally related to 4-PBA, also increases expression of ALDRP and PMP70, but not ALDP, in rats[39]. Treatment of nasal epithelia cells from cystic fibrosis patients who are homozygous or heterozygous for the ΔF508-CFTR mutation with 4-PBA results in rescue of ΔF508-CFTR from premature degradation in the endoplasmatic reticulum. It is now believed that ΔF508-CFTR protein biosynthesis is enhanced by 4-PBA because of altered regulation of protein folding by a chaperone in the endoplasmic reticulum. In X-ALD, 70% of mutations result in unstable ALDP. Thus, 4-PBA could similarly rescue unstable ALDP from premature degradation. In rodents, exposure to compounds related to 4-PBA, like clofibrate and fenofibrate, induces peroxisome proliferation[44].

SUMMARY OF THE INVENTION

It is an object of the present invention to provide methods for treating patients with adrenoleukodystrophy.

It is another object of the present invention to provide methods of screening test substances to identify candidate therapeutic agents for treating adrenoleukodystrophy.

These and other objects of the invention are achieved by one or more of the embodiments described below. In one embodiment a method is provided of treating a patient with adrenoleukodystrophy. An effective amount of an agent which causes peroxisome proliferation is administered to a patient with adrenoleukodystrophy. As a result, the level of C24:0 or C26:0 fatty acids in the central nervous system of the patient is reduced.

According to another embodiment of the invention, a method is provided for treating a patient with adrenoleukodystrophy. An effective amount of an agent which increases the activity of a peroxisomal ATP binding cassette transmembrane transporter protein in the central nervous system of the patient is administered to the patient with adrenoleukodystrophy. As a result, the level of C24:0 or C26:0 fatty acids in the central nervous system of the patient is reduced.

Another embodiment of the invention provides a method of treating a patient with adrenoleukodystrophy. An effective amount of an agent which increases beta-oxidation of C24:0 or C26:0 fatty acids in the central nervous system of the patient is administered. As a result, the level of C24:0 or C26:0 fatty acids in the central nervous system of the patient is reduced.

Also provided by the present invention are methods of screening for candidate therapeutic agents for treating adrenoleukodystrophy. In each of the methods human cells are contacted with a test substance. In one method expression of ALDRP in the human cells is measured, and a test substance which increases expression of ALDRP is identified as a candidate therapeutic agent. In another method β-oxidation of C24:0 or C26:0 fatty acids in the cells is measured, and a test substance which increases β-oxidation is identified as a candidate therapeutic agent. In yet another of the methods peroxisome number in the cells is measured, and a test substance which increases peroxisome number in the cells is identified as a candidate therapeutic agent. In still another of the methods Pex11α in the cells, and a test substance which increases Pex11α in the cells is identified as a candidate therapeutic agent.

These and other embodiments of the invention which will be described in more detail below, and which will be evident to those of ordinary skill in the art upon reading the disclosure, provide the art with therapeutic methods for treating a metabolic disease and analytic methods for identifying additional therapeutic agents which have similar modes of action.

BRIEF DESCRIPTION OF THE DRAWINGS

FIGS. 1a and b shows RT-PCR analysis of RNA levels in mouse (FIG. 1a) and human (FIG. 1b) primary fibroblasts before (−) and after (+) treatment with 5 mM 4-PBA for 2 days. The relative abundance of mRNA for the genes indicated was estimated by semi-quantitative PCR analysis using gene specific PCR primers. After exposure of both human and mouse primary fibroblasts to 5 mM 4-PBA, the relative abundance of ALDR was substantially increased compared with the RNA levels for the "housekeeping genes" GAPDH (mouse) or β-actin (human). The mRNA levels of all other genes monitored were unchanged. AOX, acyl CoA oxidase; nd, not done; bp, size of PCR product.

FIG. 5a, α-oxidation of phytanic acid in normal and X-ALD human primary fibroblasts before (filled bars) and after (hatched bars) treatment with 5 mM 4-PBA for 10 days. The increase in phytanic acid oxidation activity was significant (P<0.001 5(n=4) for X-ALD primary fibroblasts and P<0.013 (n=3) for normal primary fibroblasts).

Figure 2A:
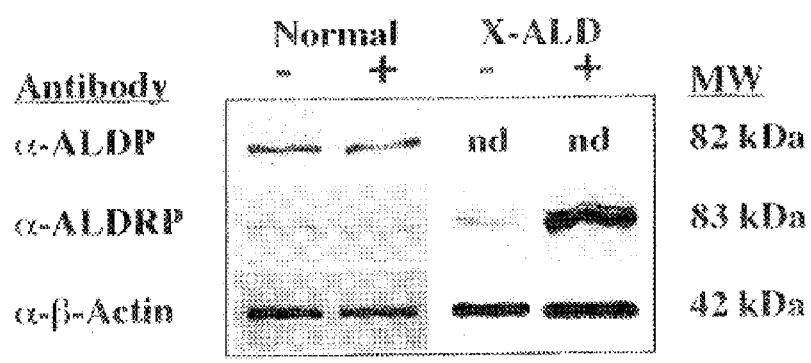
FIG. 2a shows a Western blot analysis of mouse primary fibroblasts before(−) and after (+) treatment with 5 mM 4-PBA for 5 days. nd, not detectable.

Treatment with 4-PBA for 6 weeks resulted in complete correction of C24:0 and a 78% correction of C26:0 in X-ALD mice brain, and 90% and 85% corrections of C24:0 and C26:0, respectively, in X-ALD mouse adrenal glands.

DETAILED DESCRIPTION OF THE INVENTION

We have demonstrated that 4-PBA decreases VLCFA levels by increasing VLCFA β-oxidation in cultured cells from both X-ALD patients and knockout mice. Although wild-type levels of C24:0 β-oxidation were not achieved, the resultant twofold to threefold increase was sufficient to restore normal C24:0 levels in all cell types tested. It has been shown that phenylacetate, the initial product of 4-PBA breakdown, can cross the blood-brain barrier in rats. Consistent with this is the finding that 4-PBA is effective in lowering VLCFA levels in the brain.

Our results and previous studies have established that three of the peroxisomal ABC half-transporters are at least partially functionally redundant and thus can correct VLCFA metabolism after overexpression in X-ALD cells. The activities of ALDP and ALDRP are not yet known but the equivalence of their ability to complement the VLCFA metabolic defect in X-ALD cells and their expression in different cell types indicate that they may indeed be functionally redundant. ALDR has also been proposed as a candidate for the putative X-ALD modifier gene that at least in part determines the clinical phenotype of X-ALD patients. Our demonstration of the functional equivalence of ALDP and ALDRP allows for the possibility that high expression of ALDRP in the brains of some X-ALD patients could result in VLCFA levels that are insufficient for induction of inflammatory demyelination.

Although the first measured response to 4-PBA is increased ALDRP expression coincident with increased C24:0 β-oxidation, there is a subsequent increase in peroxisome number as judged by counting immunofluorescence-stained peroxisomes and the increase in abundance of peroxisomal proteins and activity of metabolic pathways. This is a direct demonstration of a peroxisome proliferator that is effective in human cells. In mouse cells, but not human cells, there is an increase in the expression of PPARα coincident with the increase in peroxisomes. Known peroxisomal proliferators in rodents stimulate expression of both PPARα and AOX. The lack of increased AOX expression in both mouse and human cells after 4-PBA treatment indicates that the response of AOX may be independent of the PPARα response. Thus, in mouse cells, 4-PBA may induce peroxisomal proliferation through a mechanism that is common to other peroxisomal proliferators. In human cells, however, neither PPARα nor AOX expression are increased during peroxisome proliferation. Thus, it may be that the 4-PBA effect on peroxisome proliferation in humans involves an as-yet undescribed mechanism. Because peroxisomes in cells from X-ALD patients retain between 10% and 35% of wild-type VLCFA β-oxidation activity, which is not dependent on ALDP, increased numbers of peroxisomes could also contribute to improved VLCFA metabolism after treatment with 4-PBA. Because 4-PBA has been shown to affect gene expression in vivo, the molecular in vitro response documented here probably will be obtained in vivo and accounts for the effect of 4-PBA on VLCFA levels in X-ALD mice. Thus, this therapy has the potential to ameliorate or prevent the severe cerebral inflammatory demyelinating X-ALD phenotype. Overexpression of peroxisomal membrane ABC half-transporters is capable of suppressing peroxisomal membrane defects due to mutations in unrelated genes. Thus, 4-PBA treatment may have a favorable effect on several peroxisome biogenesis disorders.

Administrations of effective agents for increasing peroxisome number (causing peroxisome proliferation, increasing ABC half-transporter proteins, increasing β-oxidation of C24:0 or C26:0 fatty acids, or increasing Pex11α), can be accomplished according to any of the known means. These include without limitation, intravenous, intraperitoneal, subcutaneous, intramuscular, and oral. 4-Phenylbutyrate can be very effectively administered orally. However, the route of preferred administration will depend upon the properties of the agent. The agent can be adminstered in a free form, or complexed with other carriers or activity modifiers. For example, slow-release formulations as are known in the art may be found beneficial for increasing the average time that the agent is in contact with the target cells, organs, or organelles. Suitable dosages can be determined by routine tests. For 4-PBA, suitable dosages are in the range of 5 to 500 mg per day per weight of mouse (average weight≈20 g), preferably in the range of 10 to 100 mg per day, more preferably in the range of 50 to 75 mg per day. Appropriate adjustments on a per weight or per body surface basis for other individuals being treated can be readily made. Normally, the daily dosage for the compounds should fall in the range of 100 to 400 mg/kg body weight for children, and from 7.5 to 15 grams for adults. The size and frequency of the dosages given at any time may be varied as desired provided the indicated total daily dose is not significantly modified. The administration may be carried out intravenously or orally (e.g. in the form of sterile injectable solutions, pills, tablets, capsules, solutions, suspensions or the like). Suitable maximum dosages are those which achieve a plasma level of 3–5 mM in the plasma. Desirable plasma levels are in the range of 30 $\mu$M to 5 mM, preferably in the 300 $\mu$M to 900 $\mu$M range.

Compounds which can be used according to the present invention for treating ALD include 4-phenylbutyrate, its salts, metabolites and derivatives. These include arginine butyrate and phenylacetate. Phenylbutyrate in all mammals including man is metabolized to phenylacetate by the fatty acid beta-oxidation mechanism because the side chain is even numbered. (Lehninger, A., Biochemistry, Worth Publishers, N.Y., (1976). Other phenyl-long chain fatty acids which are metabolized to phenylacetate can also be used.

Any agent which increases the activity of a peroxisomal ATP binding cassette transmembrane transporter proteins can be used. These include both classical pharmacological agents as well as DNA molecules which encode such proteins. It has been found that ALDRP can functionally complement mutant ALDP found in adrenoleukodystrophy. Thus augmenting the number of DNA molecules in a cell which make such complementing proteins or augmenting the activity of the endogenous genes can have a beneficial effect on the patient. PMP70 and PMP69 may also be used to functionally complement mutant ALDP.

Monitoring increases and decreases in desired biological and biochemical functions can be accomplished by any of the means known in the art. These include but are not limited to the techniques enumerated below in the "methods" section of the examples. Test cells include human cells, whether normal or from adrenoleukotrophy patients. Preferably the cells are fibroblasts or lymphoblastoid cells.

The screening methods taught here can be used in conjunction with each other or singly. It is expected that such methods on cells will be followed by other test methods in whole animals and in the clinic to confirm activity and to test

EXAMPLES

Example 1

4-PBA Corrects VLCFA Levels in Cultured X-ALD Cells

We treated human primary fibroblasts and lymphoblastoid cells (EBV-transformed lymphocytes) derived from X-ALD patients with 1 mM to 7.5 mM 4-PBA and compared the results to those obtained with untreated X-ALD cells and cells from normal individuals. The genotypes of the X-ALD patients included missense, nonsense, frame shift and deletion mutations and all of the main clinical phenotypes. We found that between the concentrations of I mM and 5 mM 4-PBA, there was a dose-dependent decrease in VLCFA levels, whereas concentrations exceeding 7.5 mM were toxic for both human and mouse primary fibroblasts (data not shown).

We also analyzed VLCFA levels in primary fibroblasts from normal mice and X-ALD mice that have no detectable ALDP. We determined the effect of 5 mM 4-PBA on C24:0 and C26:0 levels in human fibroblasts, human lymphoblastoid cells and mouse fibroblasts (Table 1). After two days of treatment, a time-dependent reduction in VLCFA levels in human and mouse X-ALD cell lines was observed. In human lymphoblastoid cells and mouse fibroblasts, C24:0 and C26:0 levels were normalized within 10 days of treatment, In human X-ALD fibroblasts, C24:0 levels were normalized within 10 days, whereas C26:0 levels were reduced by 47% after 22 days. The results obtained were independent of genotype or phenotype. The difference in C26:0 response between human and mouse fibroblasts may reflect the greater initial elevation inhuman (0.46% of total fatty acids) compared with mouse (0.30% of total fatty acids) fibroblasts, rather than a difference in response to 4-PBA (these percentages are the average of those listed for untreated cell lines in Table 1).

Example 2

4-PBA Increases VLCFA (c24:0) β-oxidation

To determine if the reduction in VLCFA is caused by an increase in their degradation, we measured C24:0 β-oxidation in mouse and human X-ALD primary fibroblasts and human X-ALD lymphoblastoid cells after treatment with 4-PBA (Table 2). Exposure to 5 mM 4-PBA for 6 days resulted in a twofold to threefold increase in C24:0 β-oxidation in all X-ALD cell lines tested. Human Tibroblast C24:0 β-oxidation increased from 25% to 48% of normal; human lymphobfastoid cells, from 18% to 53% of normal; and mouse fibroblasts, from 15% to 29% of normal. Although exposure to 4-PBA did not increase β-oxidation of C24:0 to wild-type levels, the twofold to threefold increase seems to be sufficient to normalize C24:0 levels in all cell types tested, indicating a direct correlation between the decrease in VLCFA levels and the increase in VLCFA degradation. Furthermore, the increase in C24:0 β-oxidation was identical in mouse and human X-ALD primary fibroblasts, indicating an equivalent response to 4-PBA. There are several possible mechanisms that could account for the action of 4-PBA in X-ALD.

Example 3

Effect of 4-PBA on ALDP Stabilization

The response to 4-PBA (Table 1) was independent of the X-ALD genotype; cell lines assayed included a deletion of the four C-terminal exons and cell lines derived from patients with different X-ALD phenotypes. In addition, human X-ALD primary fibroblasts with destabilizing missense mutations (A626T, R660W) treated with 5 mM 4-PBA for up to 10 days did not result in detectable levels of ALDP, as determined by cytological immunofluorescence using anti-ALDP antibody (data not shown). Thus, the mechanism by which 4-PBA effects VLCFA metabolism in X-ALD cannot be through stabilization of unstable ALDP, as has been suggested for cystic fibrosis.

Example 4

Effect of 4-PBA on Functional ALDP Homologs

To monitor the effect of 4-PBA on the expression levels of the family of peroxisomal ABC half-transporter proteins (ALDRP, PMP70 and PMP69), we grew normal and X-ALD primary fibroblasts from human and mouse in the presence or absence of 5 mM 4-PBA for 2 days. Semi-quantitative RT-PCR was done on the mRNA isolated from these cells (FIG. 1). Treatment with 4-PBA resulted in a substantial increase in ALDR mRNA levels in normal and X-ALD primary fibroblasts from both human and mouse. However, exposure to 4-PBA bad little, if any, effect on the expression levels of either PMP70 or PMP69 in X-ALD or normal primary fibroblasts, or on the expression of ALDP in normal primary fibroblasts from human or mouse. In addition, the expression of acyl-CoA oxidase (AOX), the rate-limiting enzyme in VLCFA β-oxidation, was not affected. Although previous studies have reported that ALDR mRNA was not detectable in fibroblasts by either northern or RT-PCR analyses, those RT-PCR studies used about 66 ng of CDNA; we used about 250 ng of cDNA.

Figure 2B:
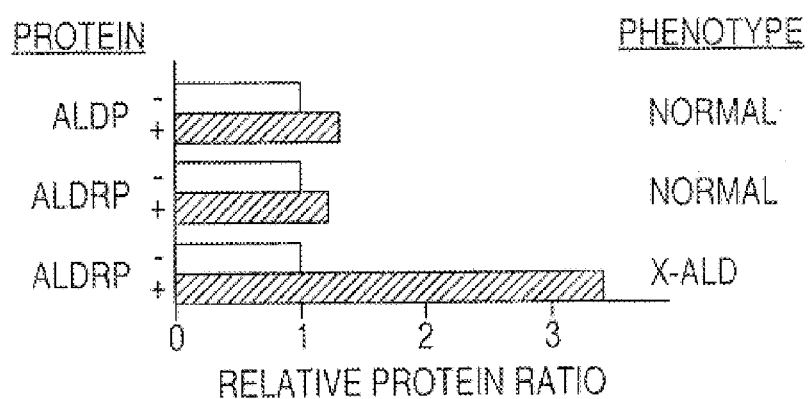
FIG. 2b shows the relative abundance of ALDRP or ALDP compared with the levels for the "housekeeping protein" β-actin present in the same preparations, by laser scanning densitometric analysis of blots in FIG. 2a. Open bars, untreated cells; hatched bars, treated cells.

Because of the inherent variability in quantitation of RT-PCR we analyzed protein levels in normal and X-ALD mouse primary fibroblasts, both untreated and treated with 4-PBA, to measure the increase in ALDRP expression. The relative ALDRP levels in both normal and X-ALD fibroblasts and ALDP in normal fibroblasts were determined by comparing their abundance with that of the protein of the housekeeping gene β-actin in the same samples after densitometric analysis of western blots (FIG. 2). In agreement with the RT-PCR results, treatment with 4-PBA dia not alter the relative level of ALDP in normal mouse fibroblasts. However, ALDRP levels were increased in X-ALD fibroblasts (by 3.4-fold) but not in normal fibroblasts, even though mRNA levels were increased in both. These findings indicate that ALDP1 and ALDRP may occupy equivalent domains within the peroxisomal membrane. This would agree with the observation that ALDP and ALDRP are generally expressed in different cell types. Although ALDRP was not increased in normal fibroblasts after 10 days of exposure to 4-PBA (data not shown), it is possible that even longer exposures would result in increased levels of ALDRP in normal fibroblasts because of turnover of ALDP.

Example 5

ALDR cDNA Complementation Restores C24:0 β-oxidation

Figure 3:
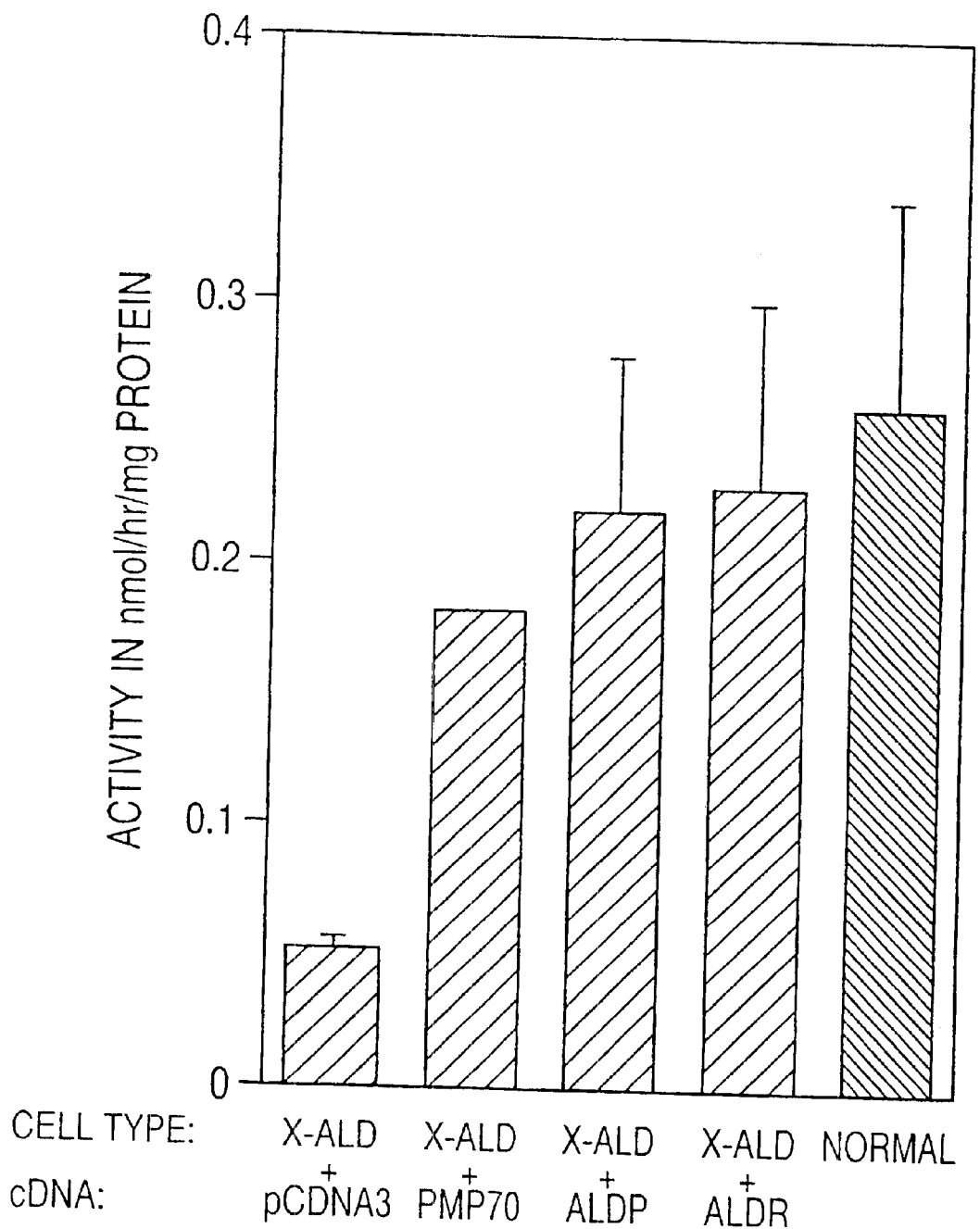
FIG. 3 shows peroxisomal ABC half-transporter complementation of C24:0 β-oxidation. Human X-ALD fibroblasts transformed with SV40 T antigen were transfected with recombinant expression vector (pCDNA3) alone or with vector containing cDNA for PMP70, ALDP or ALDRP (hatched bars). The rates of C24:0 β-oxidation in the transfected cells were corrected for the fraction of cells expressing the transgene, as determined by immunofluorescence staining of the transgene. The adjusted rates were compared with the rates of C24:0 β-oxidation determined in transformed fibroblasts from normal individuals (filled bar). The increase in C24:0 β-oxidation after expression of ALDRP cDNA provides an explanation for the normalization of C24:0 levels in X-ALD cells after treatment with 4-PBA. Duplicate measurements were done for each transfection. The indicated values are the mean and standard deviation for pCDNA3, n 6; ALDP, n=5: ALDRP, n=4; and normal, n=5. PMP70, n=1.

Expression of either ALDP or PMP70 CDNA in X-ALD fibroblasts increases C24:0 β-oxidation. To determine if increased ALDR expression could account for increased C24:0 β-oxidation and the restoration of C24:0 levels after 4-PBA treatment, we overexpressed ALDRP CDNA in cultured transformed fibroblasts from X-ALD patients. We analyzed the resulting C24:0 β-oxidation activity in X-ALD fibroblasts complemented with vector (pCDNA3), PMP70, ALDP or ALDRP CDNA (FIG. 3). Overexpression of each of the peroxisomal ABC half-transporters tested increased C24:0 β-oxidation, and both ALDRP and ALDP resulted in activity near that observed in transformed normal fibroblasts. Thus, increased expression of ALDR after exposure of X-ALD cells to 4-PBA provides an explanation for the reduction of VLCFA levels.

Example 6

Effect of 4-PBA on Peroxisomal Proliferation

Figures 4A, 4B:
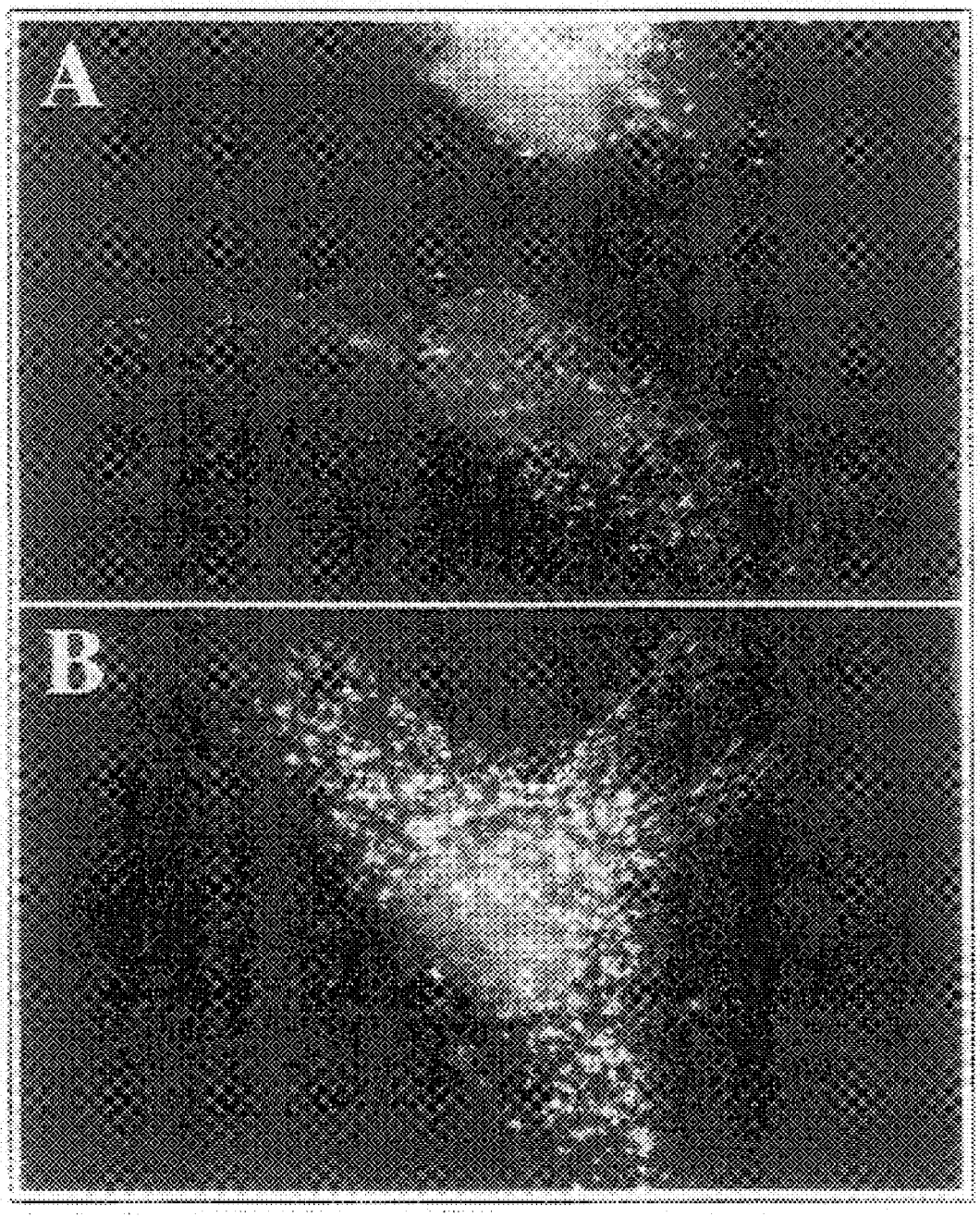
FIGS. 4a and b shows peroxisomal staining in human X-ALD primary fibroblasts. Punctate staining peroxisomes in human X-ALD primary fibroblasts were seen using immunofluorescence analysis with a polyclonal antibody against the C-terminal tripeptide peroxisomal targeting signal I (present in most peroxisomal matrix proteins) before (FIG. 4a) and after (FIG. 4b) 10-day treatment with 5 mM 4-PBA. Counting the number of peroxisomes per cell indicated a 2.4-fold increase (P<0.0000001) after treatment.

Although human cells generally do not respond to agents known to function as peroxisome proliferators in other species[44], 4-PBA may function as a peroxisome proliferator in humans. To determine if 4-PBA induces peroxisome proliferation, we initially examined untreated and treated human X-ALD primary fibroblasts. Peroxisomes were made visible with immunofluorescence using a polyclonal antibody to the C-terminal tripeptide (SKL) peroxisome targeting signal 1 (PTS1), which is present in most peroxisomal matrix proteins. Cells were assayed after 5, 8 and 10 days of exposure to 5 mM 4-PBA. As seen by immunofluorescence, there was an approximately twofold increase in peroxisome number after 8 days of treatment (FIG. 4). We counted the peroxisomes after 10 days of treatment (Table 3). Slides were scanned visually and cells categorized as having low, medium or high numbers of peroxisomes. For each cell line, the number of peroxisomes is the mean of three 'low', four 'medium' and three 'high' cells (Table 3). There was no difference between control cells and X-ALD cells in either the number of peroxisomes per cell or in the response to 4-PBA. The combined results from five X-ALD cell lines and four control cell lines were 416±27 peroxisomes per cell before exposure to 4-PBA and 1014±108 after exposure. The 2.4-fold increase in the number of peroxisomes per cell was statistically significant ($P<0.0000001$, two-tailed Student's t-test). Peroxisome numbers obtained with an antibody against a peroxisomal membrane protein (Pex14p) gave similar results (data not shown).

Figure 5A:
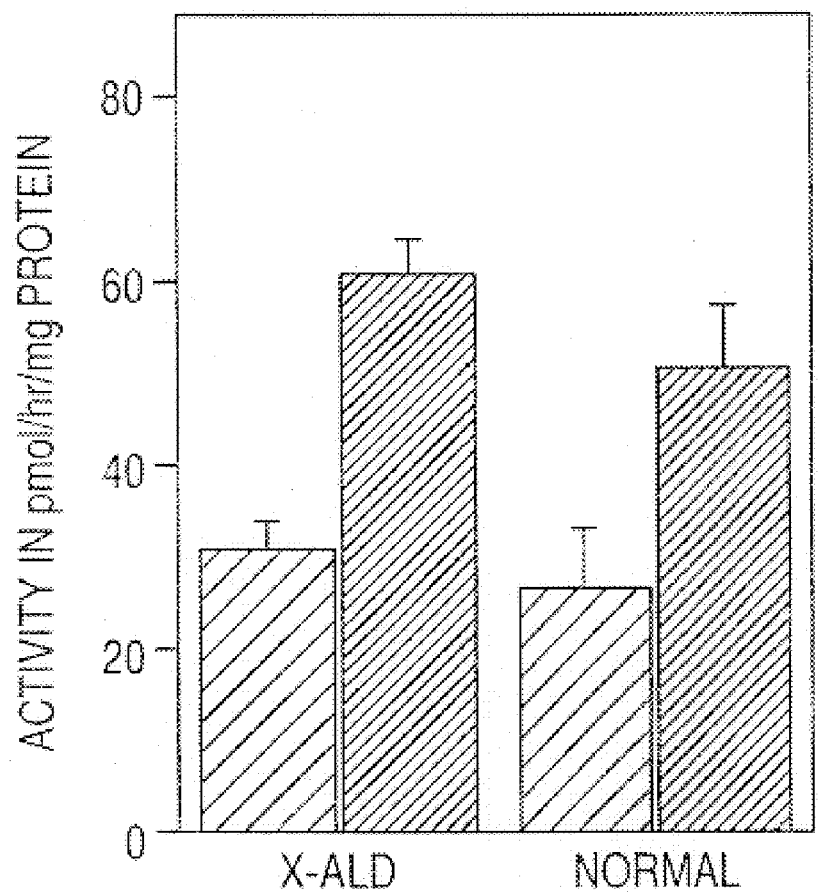
FIGS. 5a and b shows peroxisome function after treatment with 4-PBA.
Figure 5B:
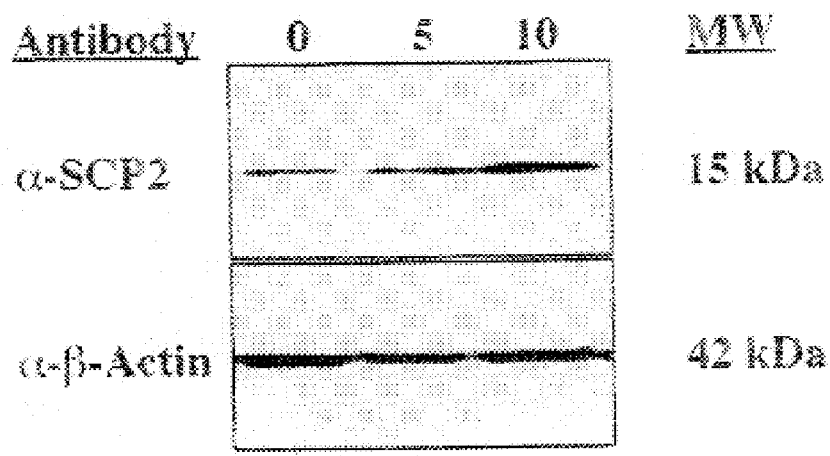
FIG. 5b, protein levels of SCP2 (the peroxisomal matrix-specific sterol carrier protein 2) were determined in human X-ALD primary fibrobalsts after exposure to 4-PBA for 0, 5 or 10 days, using western blot and densitometric analysis. The relative amount of SCP2 protein was compared to the housekeeping gene β-actin. Exposure to 4-PBA resulted in a substantial (approximately threefold) increase in SCP2, consistent with the increase in peroxisome numbers.

To determine if the increase in peroxisome number resulted in an increase in peroxisome function, we examined peroxisomal components that are not affected in X-ALD: phytanic acid oxidation and levels of the peroxisomal matrix protein sterol carrier protein 2 (SCP2). Phytanic acid oxidation occurs exclusively in the peroxisomal matrix and can therefore serve as a marker for peroxisomal function. Treatment of either X-ALD or normal human primary fibroblasts resulted in a twofold increase in phytanic acid oxidation, in agreement with the increased number of peroxisomes estimated by immunofluorescence (FIG. 5a). SCP2 is a 15-kDa protein located exclusively in the peroxisomal matrix. We determined its abundance in human X-ALD fibroblasts by western blot analysis before and after 5 and 10 days of exposure to 5 mM 4-PBA. There was a significant increase in the amount of SCP2, again consistent with a approximately twofold induction of peroxisomes (FIG. 5b). Because peroxisomes in X-ALD cells have a residual VLCFA β-oxidation activity that is independent of ALDP, 4-PBA stimulation of peroxisome proliferation increases an alternative metabolic pathway in addition to a functionally redundant gene.

Figure 6A:
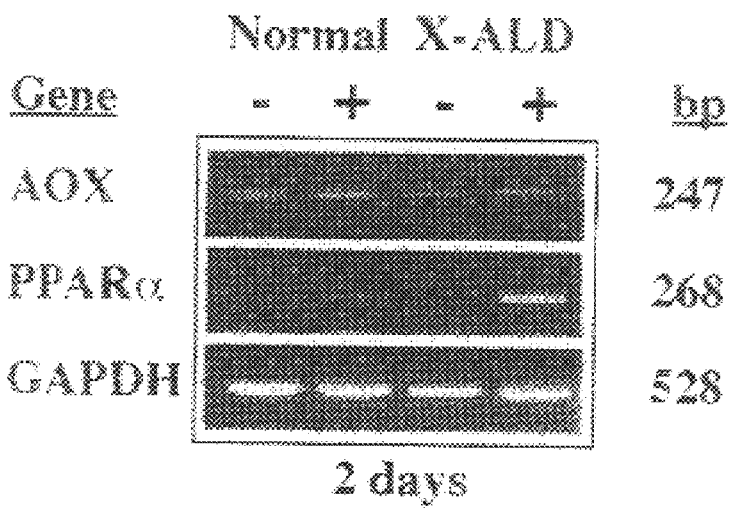
FIGS. 6a, b and c shows RT-PCR analysis of RNA levels, in mouse primary fibroblasts after 2 days of treatment with 5 mM 4-PBA (FIG. 6a) and in human primary fibroblasts after 2 days (FIG. 6b) or 10 days (FIG. 6c) of treatment with 5 mM 4-PBA. The relative abundance of RNA for each gene indicated was estimated by semi-quantitative PCR analysis using gene-specific PCR primers. Compared with the RNA levels for the "housekeeping gene" GAPDH (mouse) or β-actin (human), AOX levels were unchanged in both mouse and human primary fibroblasts treated with 4-PBA, whereas PPARα RNA was increased in mouse fibroblasts but not in human fibroblasts. Pex11α expression was substantially increased in human fibroblasts after two days.
Figure 6B:
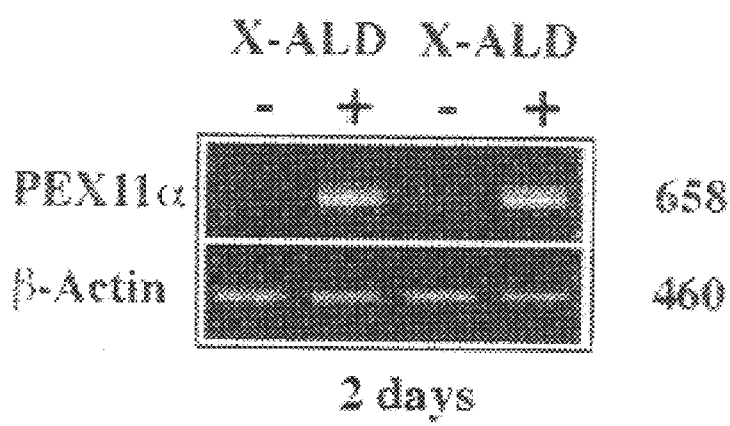
Figure 6C:
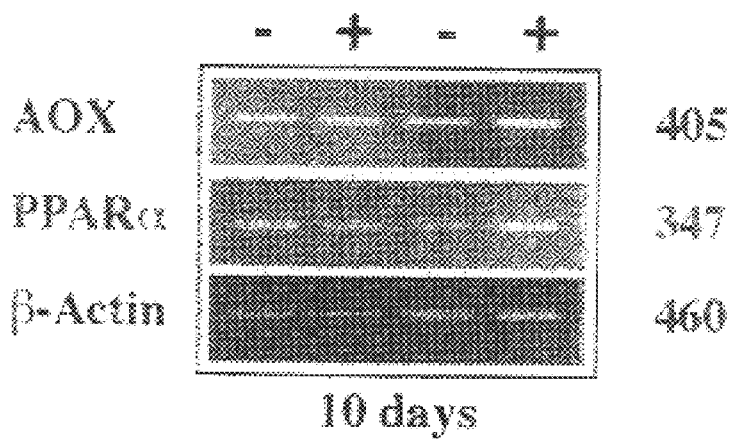

To analyze the mechanism of 4-PBA-induced peroxisome proliferation in human cells, we examined the expression of Pex11a, the inducible regulator of peroxisome abundance; peroxisome proliferator-activated receptor a (PPARα), the receptor for peroxisome proliferators; and AOX, a gene whose expression in rodents is considerably increased during peroxisome proliferation (FIG. 6). Pex11 has been shown to be upregulated during peroxisome proliferation in yeast, and in rodents Pex11 is variably expressed in different tissues and shows increased expression in rat liver after treatment with peroxisome proliferators. By RT-PCR analysis, Pex11α transcripts were undetectable in normal or X-ALD mouse fibroblasts either before or after 10 day exposure to 5 mM 4-PBA (data not shown). In contrast, treatment of human fibroblasts resulted in a substantial increase in Pex11α expression after 2 days.

In rodents PPARα expression is increased by peroxisomal proliferators. Semi-quantative RT-PCR analysis of PPARα expression showed that its expression is increased in mouse X-ALD fibroblasts as early as 2 days after treatment, but its expression in human X-ALD fibroblasts is unchanged, even after 10 days of treatment, when peroxisome proliferation is already observed. Thus, although the peroxisome proliferation response in mice may be, at least in part, through the documented PPARα pathway, the response in human cells seems to be through a newly discovered pathway that may involve Pex11α. We also examined the expression of AOX which in rodents is also increased by most peroxisome proliferators. AOX expression in both mouse and human fibroblasts was unchanged after 2 days of exposure to 5 mM 4-PBA and remained unchanged in human fibroblasts after 10 days of exposure. This again indicates a newly discovered pathway for 4-PBA-induced peroxisome proliferation in humans and perhaps in rodents. AOX has been identified as the rate-limiting step in VLCFA β-oxidation. Treatment with 4-PBA increases VLCFA β-oxidation in X-ALD cells, but not to the levels observed in normal cells. Thus, the lack of increased AOX expression after 4-PBA treatment will not limit the restoration of VLCFA β-oxidation to at least normal levels.

Example 7

In Vivo Efficacy of 4-PBA

Figure 7:
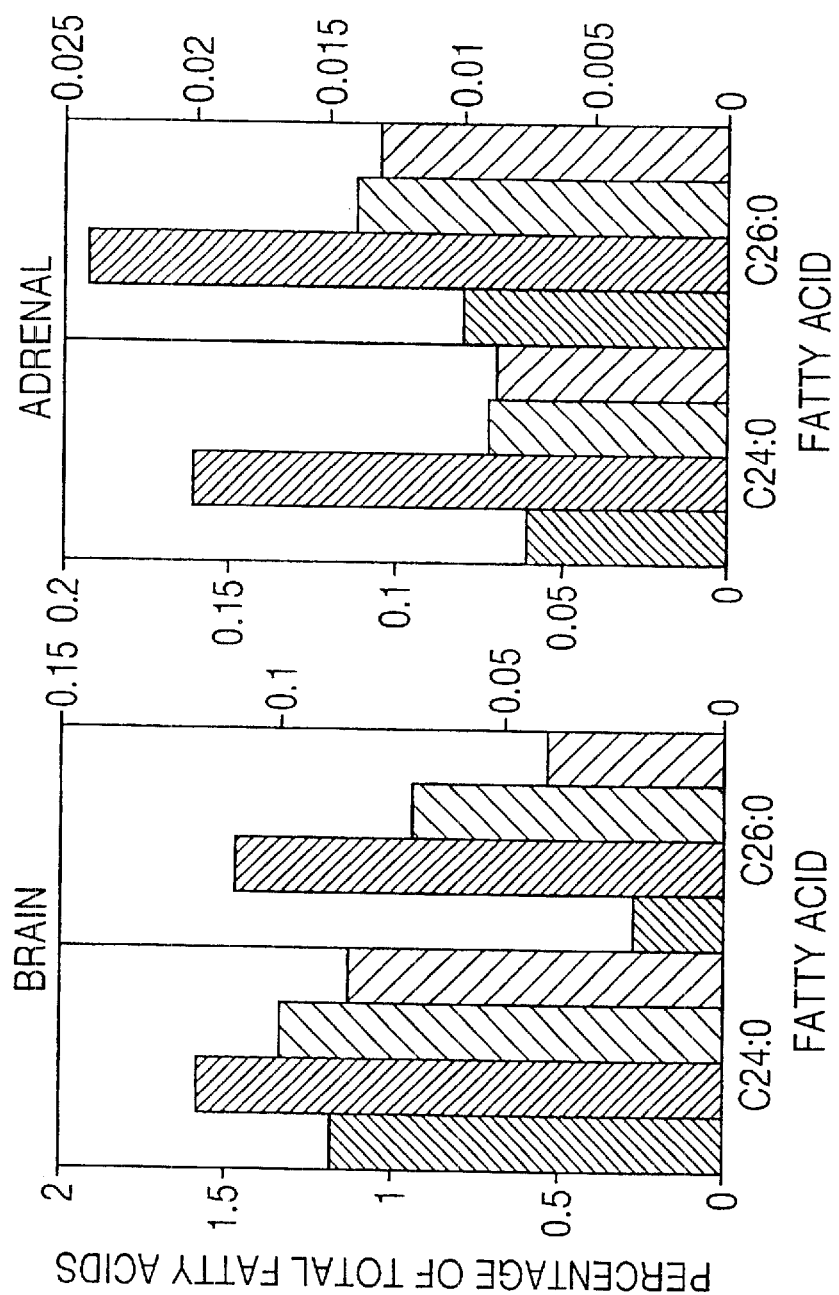
FIG. 7 shows in vivo efficacy of 4-PBA. VLCFA analyses of mouse brains and adrenal glands from control mice (black bars; n=4 for brain and n=6 for adrenal gland), untreated X-ALD mice (grey bars; n=4 for brain and n=7 for adrenal gland), and X-ALD mice treated with 4-PBA for 4 weeks (right hatched bars; n=2) or 6 weeks (left hatched bars; n=2). Dietary 4-PBA treatment for 4 weeks resulted in a substantial reduction in both brain and adrenal gland VLCFA levels.

To measure the in vivo efficacy of 4-PBA, we supplemented mouse chow and water with 4-PBA. X-ALD mice were on the 4-PBA diet for 4 and 6 weeks. We determined the effect of 4-PBA on VLCFA levels in mouse brain and adrenal glands (FIG. 7). Four weeks of dietary 4-PBA treatment resulted in substantial reduction of C24:0 and C26:0 levels in both brain and adrenal glands. Six weeks of dietary 4-PBA treatment resulted in complete normalization of brain C24:0 and 80% normalization of brain C26:0 levels and approximately 90% correction of both C24:0 and C26:0 in the adrenal glands.

Methods Used in Examples:

Cell culture and 4-PBA treatment. Cell lines derived from X-ALD patients and X-ALD mice were grown in MEM (fibroblasts) or RPMI (ymphoblastoid cells) supplemented with fetal calf serum (10%), penicillin (100 U/ml), streptomycin (100 U/mi) and glutamine (2 mM). On day 0, cells were divided into two separate tissue culture flasks, and 4-PBA (5 mM final concentration, diluted from a 0.5 M stock solution in PBS, pH 7.6: Mediatech, Grand Island, N.Y.) was added to one flask. Cells in the second flask were grown without drug for the same length of time and served as controls. The media were changed every 3–4 days.

Cultured cells were mixed cell lines from X-ALD patients with different mutations, including missense (R591 Q S606L, A626T, R66OW), nonsense (Q64SX), an in-frame amino acid deletion (E291 del), an identical frame shift (fs E471) in two independent cell lines, one from a patient with CCER and one from a patient with the Addison-only phenotype, and a large deletion in the COOH-terminal half of ALDP (exon 7-1 Odel); and with different phenotypes, including CCER. AMN and Addison-only. Two of the X-ALD cell lines have detectable ALDP (R591 Q S606L), whereas all of the other cell lines have no detectable ALDP.

In vivo delivery of 4-PBA to X-ALD mice. 4-PBA was delivered to X-ALD mice in their regular chow and water. 4-PBA chow was prepared by B'OServ (Holton Industries, Frenchtown, N.J.). 7.5 gram of 4-PBA (Buphenyl; provided by Ucyclyd Pharma, Ucyclyd Pharma, Glen Burnie, Md.) was mixed into each kilogram of Purina Rodent Diet 5001 (BioServ; Holton Industries, Frenchtown, N.J.) before they were shaped into half-inch pellets. 4-PBA chow in the form of half-inch pellets that had not been autoclaved was used to feed X-ALD mice. In addition, the water for the X-ALD mice on the 4-PBA diet contained 1 0 grams of 4-PBA per liter. The daily 4-PBA uptake was estimated to be 70 mg of 4-PBA, based on 4 grams of food and 4 ml of water intake per day. Mice were killed after 4 or 6 weeks on the 4-PBA diet. Brains and adrenal glands from normal LD and X-ALD/4-PBA mice were collected for VLCFA analysis as described.

Biochemical measurements. Tissue culture cells were grown in the presence or absence of 5 mM 4-PBA, collected from tissue culture flasks using trypsin, washed twice with PBS and subjected to biochemical analysis. For VLCFA measurements, total lipids were extracted, converted to methyl esters, purified by TLC and subjected to capillary GC analysis as described. Duplicate assays were set up independently and were assayed on different days. C24:0 β-oxidation activity of human and mouse fibroblasts and human lymphoblastoid cells was determined by measuring their capacity to degrade [1-$^{14}$C]-C24:0 fatty acid (American Radiolabeled Chemicals, St Louis, Mo.) to water-soluble products as described. Phytanic acid oxidation was measured as described. Cells were incubated with [2,3-$^{3}$H]-phytanic acid for 24 hours, and the release of $^{3}$H-$H_2O$ to the aqueous medium was determined (activity in pmol/hr per mg protein). The statistical significance of measured biochemical differences between untreated and 4-PBA treated X-ALD cell lines was determined by the two-tailed Student's t-test For transfection studies with recombinant expression vector (pCDA3) alone or with vector containing cDNA for PMP70, ALDP or ALDRP, human X-ALD fibroblasts were transformed with SV40 T antigen as described.

Semi-quantitative RT-PCR analysis. Total RNA from tissue culture cells ($10^6$–$10^7$ cells/sample) was isolated using TRizol Reagent™ (Life Technologies), treated with DNase I (100–200 units in 40 mM HCI, 10 mM NaCl, 6 mM $MgCl_2$, pH 7.3), incubated at 37° C. for 30 min, extracted with phenol/chloroform, and precipitated with isopropanol. cDNA was generated using MMLV reverse transcriptase (RT) (Life Technologies). PCR was done in the linear range of amplification (determined for each primerpair-cDNA combination). For each cDNA sample, a 'cocktail' was prepared, containing PCR buffer (Promega), 200 gM of each DNTP, 1.5 mM $MgCl_2$, 250 ng cDNA, 0.25 U of Taq polymerase (Promega) and 50o/o DMSO. The 'cocktail' was divided into separate tubes containing cDNA specific primers.

Primers. The PCR primers used are listed below. In the parentheses, h indicates human and m, mouse; this is followed by the gene name, product size and annealing temperature. For primer sequences, F is forward and R is reverse. (hALD, 249, 64° C.)F: 5'-GGAGCTGGTGGCAGAGGA-3', R: 5'-ACAGCCACCATGAGCAGG-3'; (mALD, 526, 59° C.) F: 5'-CCTATCATCACACCCACTGGAGAG-3', R: 5'-GCAGTGCGATACCAGCATCMG-3'; (hPMP70, 405, 60° C.) F: 5'-TTTGAAGTTCGATCTGGG-3', R: 5'-ATCCAAAATGGCAAACTGGG-3'; (mPMP70, 405, 60° C.) F: 5'-TTrGAAGTTCGATCTGGG-3', R: 5'-ATCCAAAATGGCAAACTGGG-3'; (hALDR, 312,56° C.) F: 5-GCTGTCAGCATTGATGTCGAAGGA-3', R: 5'-TTAAGATGTCTCATC-3'; (mALDR, 711, 57° C.) F: 5'-TGGTGGCTTCCAGGCTAAACTTC-3', R: 5'-CCGAGTCTTCCCCCAGAATTT'TG-3'; (hPMP69, 319, 60° C.) F: 5'-CTCACTGAGCACCTTCACCG-3', R: 5-CTCCCTCCAGCTTCTCCTGA-3'; (hAOX 405, 60° C.) F: 5'-CAGCCACGTATGACCCTGAA-3', R: 5'-CTCCCACAAGGAAGGACCTG-3'; (mAOX, 247, 60° C.) F: 5'-TCACGCACGTCTrGGATGGTAGTC-3', R: 5'-CCAACAGGTTCCACAAAATTGACC-3'; (hPPAR a, 347, 60° C.) F: 5-AGAGCCCGTrATCTGAAGAGTrCC-3', R: 5'-CACCAGCTTGAGTCGAATCGTTC-3'; (mPPARa, 268, 60° C.) F: 5'-GATTrCTCAGTCCATCGG-TGAGG-3, R: 5'-GAAGCCCTTACAGCCTTCACATG-3'; (hpex11α658, 55° C.) F: 5-CCCGTCGACGGACGCCTTCACCCGCTTCACC-3', R: 5'-CCACGCGGCCGCTCACAGCTGGTCCAAAGG GTTCAGG-3'; (mpex11α, 720, 55° C.) F: 5'-CCCGGTACCATGGACGCCTrCATCCGAGTCGCC-3', R: 5'-CCCGGATCCGCGGGCCTTCAGTT'TCAGCTGAGG-3'; (β-Actin, 460, 62° C.) F:5'-TTTGAGACCTTCAACACCCCAG-3', R: 5'-TTTCGTGGATGCCACAGGA-3, (glyceraldehyde 3-phosphate dehydrogenase (GAPDH), 528, 62° C.) F: 5'-ACCACCATGGAGAAGGCTGG-3, R: 5'-CTCAGTGTAGCCCAGG'ATGC-3'. β-Actin and GAPDH primers were used for both human and mouse analyses.

Western blot analysis. Tissue culture cells were scraped from tissue culture dishes using a policeman, into cold PBS solution and protease inhibitor cocktail (Boehringer). Samples were mixed (1:1) with 2× sample buffer. Total protein samples were fractionated by SDS-PAGE using a 7.5% gel using the method of Laemmlis'. Proteins were transferred to a polyvinylidene fluoride membrane (immobilon-P; Miffipore, Bedford, Mass.) for 2 hours at 24 V. Immunoblot analysis used antibodies against β-actin (Sigma), mouse ALDP and mouse ALDRP (anti-ALDP and anti-ALDRP were a gifts from P. Aubourg) and human SCP2 (SCP2 antibody was a gift from J. Strauss). Enhanced chemiluminescence (SuperSignal Substrate; Pierce, Rockford, Ill.) was used to detect bound antibody.

Immunofluorescence and peroxisome counting. Human skin fibroblasts were grown on cover slips in the presence or absence of 5 mM 4-PBA, and indirect immunofluorescence was done as described. The anti-SKL (PTSI) antibody was a gift from S. Gould and the anti-Pex11α antibody was a gift from S. Mihalik. To count peroxisomes, we photographed immunofluorescence-stained cells after focusing on the cell nucleus, and determined the peroxisome number per cell with the aid of a colon counter after projecting the slides to enlarge the image.

References

1. Cooke, J., Nowak, M. A., Boerlijjst, M. & Maynard-Smith, J. Evolutionary origins and maintenance of redundant gene expression during metazoan development. *Trends Genet* 13, 360–364 (1997).

2. Thomas, J. H. Thinking about genetic redundancy. *Trends Genet* 9, 395–399 (1993).
3. Charache, S. et al. Treatment of sickle cell anemia with 5-azacytidine results in increased fetal hemoglobin production and is associated with nonrandom hypomethylation of DNA around the gamma-delta-beta-globin gene complex. *Proc Natl Acad Sci USA* 80, 4842–4846 (1983).
4. Dover, G. J. et al. Hydroxyurea induction of hemoglobin F production in sickle cell disease: relationship between cytotoxicity and F cell production. *Blood* 67, 735–738 (1986).
5. Perrine, S. P. et al. A short-term trial of butyrate to stimulate fetal-globin-gene expression in the beta-globin disorders [see comments]. *N Engl J Med* 328, 81–86 (1993).
6. Dover, G J., Brusilow, S. & Charache, S. Induction of fetal hemoglobin production in subjects with sickle cell anemia by oral sodium phenylbutyrate. *Blood* 84, 339–343 (1994).
7. Tinsley, J. M. et al. Amelioration of the dystrophic phenotype of mdx mice using a truncated utrophin transgene [see comments]. *Nature* 384, 349–353 (1996).
8. Roush, W. Backup gene may help muscle help themselves [news]. *Science* 276, 35 (1997).
9. Wanders, R. J. et al. Direct demonstration that the deficient oxidation of very long chain fatty acids in X-linked adrenoleukodystrophy is due to an impaired ability of peroxisomes to activate very long chain fatty acids. *Biochem Biophys Res Commun* 153, 618–624 (1988).
10. Lazo, O., Contreras, M., Bhushan, A., Stanley, W. & Singh, I.
Adrenoleukodystrophy: impaired oxidation of fatty acids due to peroxisomal lignoceroyl-CoA ligase deficiency. *Arch Biochem Biophys* 270, 722–728 (1989).
11. Moser, H. W., Smith, K. D. & Moser, A. B. X-linked adrenoleukodystrophy in *The Mateabolic Basis of Inherited Disease* 7th edn (eds Scirver, C. R., Baeudet, A. L., Sly. W. W. S. & Valle, D.) 4256–4300 (McGraw Hill, New York, 1995).
12. Powers, J. M. Adreno-leukodystrophy (adreno-testiculo-leukomyeloneuropathic-complex). *Clin Neuropathol* 4, 181–199 (1985).
13. Mosser, J. et al. Putative X-linked adrenoleukodystrophy genes shares unexpected homology with ABC transporters. *Nature* 361, 726–730 (1993).
14. Kemp, S. et al. Idnetification of a two base pair deletion in five unrelated families with adrenoleukodystrophy: a possible hot spot for mutations. *Biochemm Biophy Res Commun* 202, 647–653 (1994).
15. Kok, F. et al. Mutational analysis of patients with X-linked adrenoleukodystrophy. *Hum Mutat* 6, 104–115 (1995).
16. Mosser, J. et al. The gene responsible for adrenoleukodystrophy encodes a peroxisomal membrane protein. *Hum Mol Genet* 3, 265–271(1994).
17. Ligtenberg, M. J. et al. Spectrum of mutations in the gene encoding the adrenoleukodystrophy protein. *Am J Hum Genet* 56, 44–50 (1995).
18. Feigenbaum, V. et al. Mutational and protein analysis of patients and heterozygous women with X-linked adreno-leukodystrophy. *Am J Hum Genet* 58, 1135–1144 (1996).
19. Krasemann, E. W., Meier, V., Korenke, G. C., Hunnema, D. H. & Hanefeld, F. Identification of mutations in the ALD-gene of 20 families with adrenoleukodystrophy/adrenomyeloneuropathy. *Hum Genet* 97, 194–197 (1996).
20. Cartier, N. et al. Retroviral-mediated gene transfer corrects very-long-chain fatty acid metabolishm in adrenoleukodystrophy fibroblasts. *Proc. Natl Acad Sci USA* 92, 1674–1678 (1995).
21. Braiternan, L. T. et al. Suppression of peroxisomal membrane protein defects by peroxisomal ATP binding cassette (ABC) proteins. *Hum Mol Genet* 7 239–247 (1998).
22. Lombard-Platet, G., Savary, S., Sarde, C. O., Mandel. J. L. & Chimini, G. A. close relative of the adrenoleukodystrophy (ALD) gene codes for a peroxisomal protein with a specific expression pattern. *Proc Natl Acad Sci USA* 93, 1265–1269 (1996).
23. Holzinger, A., Kammerer, S., Berger, J. & Roscher. A. A. cDNA cloning and mRNA expression of the human adrenoleukodystrophy related protein (ALDRP), a peroxisomal ABC transporter. *Biochem Biophys Res Commun* 239, 261–264 (1997).
24. Kamijo, K., Taketani, S., Yokota. S., Osumi, T. & Hashimoto. T. The 70-kDa peroxisomal membrane protein is a member of the Mdr (P-glycoprotein)-related ATP-binding protein superfamily. *J Biol Chem* 265, 4534–4540 (1990).
25. Gartner, J., Moser, H. & Valle, D. Mutations in the 70K peroxisomal membrane protein gene in Zellweger syndrome. *Nat Genet* 1, 16–23 (1992).
26. Shani, N., Jimenez-Sanchez, G. Steel. G., Dean. M. & Valle. D. Identification of a fourth half ABC transporter in the human peroxisomal membrane. *Hum Mol Genet* 6, 1925–1931 (1997).
27. Holzinger, A., Kammerer, S. & Roscher. A. A. Primary structure of human PMP69, a putative peroxisomal ABC-transporter. *Biochem Biophys Res Commun* 237, 152–157 (1997).
28. Boles, D. J., Craft, D. A., Padgett, D. A., Loria, R. M. & Rizzo, W. B. Clinical variation in X-linked adrenoleukodystrophy: fatty acid and lipid metabolism in culture fibroblasts. *Biochem Med Metab Biol* 45, 74–91 (1991).
29. Lu, J. F. et al. A mouse model for X-linked adrenoleukodystrophy. *Proc. Natl Acad Sci USA* 94, 9366–9371 (1997).
30. Loes, D. J. et al. Childhood cerebral form of adrenoleukodystrophy: short-term effect of bone marrow transplantation on brain MR observation. *AJNR Am J Neuroradiol* 15, 1767–1771 (1994).
31. Moser, H. W. Adrenholeukodystrophy: phenotype, genetics, pathogenesis and therapy. *Brain* 120, 1485–1508 (1997).
32. Poulos, A., Gibson, R., Sharp, P., Beckman, K. & Grattan-Smith, P. Very long chain fatty acids in X-linked adrenoleukodystrophy brain after treatment with Lorenzo's oil. *Ann Neurol* 36, 741–746 (1994).
33. Rasmussen, M., Moser, A. B., Borel, J., Khangoora, S. & Moser, H. W. Brain, liver, and adipose tissue erucic and very long chain fatty acid levels in adrenoleukodystrophy patients treated with glyceryl trierucate and trioleate oils (Lorenzo's oil). *Neurochem Res* 19, 1073–1082 (1994).
34. Maestri, N. E., Brusilow, S. W., Clissold, D. B. & Bassett. S. S. Long-term treatment of girls with ornithine transcarbamylase deficiency. *N Engl J Med* 355, 855–859 (1996).
35. Carstea, E. D., Murray, G. J. & O'Neill, R. R. Molecular and finctional characterization of the murine glucocerebrosidase gene. *Biochem Biophys Res Commun* 184, 1477–1483 (1992).

36. Deng, G., Liu, G., Hu, L., Gum, J. R, jJr. & Kim. Y. S. Transcriptional regulation of the human placental-like alkaline phosphatase gene and mechanisms involved in its induction by sodium butyrate. *Cancer Res.* 52 3378–3383 (1992).
37. Fregeau, C. J., Helgason, C. D. & Bleackley, R. C. Two cytotoxic cell proteinase genes are differentially sensitive to sodium butyrate. *Nucleic Acids Res* 20, 3113–3119 (1992).
38. Liu, L., Hudgins, W. R., Miller, A. C., Chen. L. C. & Smid. D. Transcriptional upregulation of TGF-alpha by phenylacetate and phenylbutyrate is associated with differentiation of human melanoma cells. *Cytokine* 7, 449–456 (1995).
39. Albet, S. etal. Fenofibrate differently alters expression of genes encoding ATP-binding tmasporter proteins of the peroxisomal membrane. *FEBS Lett* 405, 394–397 (1997).
40. Rubenstein, R. C., Egan, M. E. & Zeitin, p. L. In vitro pharmacologic restorationn of CFTR-mediated chloride transport with sodium 4-phenylbutyrate in cystic fibrosis epithelial cells containing delta F508-CFTR. *J Clin Invest* 100, 2457–2465 (1997).
41. Rubenstein, R. C. & Zeitlin, P. L. A pilot clinical trial of oral sodium 4-phenylbutyrate (Buphenyl) in deletaF508-homozygous cystic fibrosis patients: parital restoration of nasal epithelial CFTR function. *Am J Respir Crit Care Med* 157, 484–490 (1998).
42. Watkins, P. A. et al. Altered expression of ALDP in X-linked adrenoleukodystrophy. *Am J Hum Genet* 57, 292–301 (1995).
43. Kemp, S. et al. ALDP expression in fibroblasts of patients with X-linked adrenoleukodystrophy. *J Inherit Metab Dis* 19, 667–674 (1996).
44. Reddy, J. K., Suga, T., Mannaerts, G. P., Lazarow, P. B. & Subramani, S.
    Peroxisomes: Biology and role in toxicology and disease. in *Annals of the new York Academy of Sciences* Vol. 804 (eds Boland, B., Cullinan, J., Cullinan, D. M. & Garry, M. L.) 801 (New York Academy of Sciences, New York, 1996).
45. Pineau, T. et al. Activation of a human peroxisome proliferator-activated receptor by the antitumor agent phenylacetate and its analogs. *Biochem Phharnacol* 52, 659–667 (1996).
46. Aoyama, T., Souri, M., Kamijo, T., Ushikubo, S. & Hashimoto, T.
    Peroxisomal acyl-coenzyme A oxidase is a rate-limiting enzyme in a very-long-chain fatty acid beta-oxidation system. *Biochem Biophys Res Commun* 201, 1541–1547 (1994).
47. Fouquet, F. et al. Expression of the adrenoleukodystrophy protein in the human and mouse central nervous system. *Neurobiol Dis* 3, 271–284 (1997).
48. Gould, S. J., Krisans, S., Keller, G. A. & Subramani, S. Antibodies directed against the peroxisomal targeting signal of firefly luciferase recognize multiple mammalian peroxisomal proteins. *J Cell Biol* 110, 27–34 (1990).
49. Mihalik, S. J. et al. Identification of PAHX, a Refsum disease gene. *Nat Genet* 17, 185–189 (1997).
50. Ohba, T. et al. The structure of the human sterol cqarrier protein X/sterol carrier protein 2 gene (SCP2). *Genomics* 24, 370–374 (1994).
51. Sakai, Y. et al. The *Candida boidinii* peroxisomal membrane protein Pmp 30 has a role in peroxisomal proliferation and is functionally homologous to Pmp27 from *Saccharomyces cerevisiae*. *J Bacteriol* 177, 6773–6781 (1995).
52. Erdmann, R. & Blobel, G. giant peroxisomes in oleic acid-induced *Saccharomyces cerevisiae* lacking the peroxisomal membrane protein Pmp27p. *J Cell Biol* 128, 509–523 (1995).
53. Ram, Z, et al. Growth inhibition, tumor maturation, and extended survival in experimental brain tumors in rats treated with phenylacetate. *Cancer Res* 54, 2923–2927 (1994).
54. Moser, H. W. & Moser, A. B. Measurement of saturated very long chain fatty acids in plasma in *Techniques in Diagnostic Biochemical Genetics: A Laboratory Manual* (ed. A., H. F.) 177–191 (Wiley-Liss, New York, 1991).
55. Watkins, P. A., Ferrell, E. V., Jr., Pedersen, J. I. & Hoefler, G. Peroxisomal fatty acid beta-oxidation in HepG2 cells. *Arch Biochem Biophy* 289, 329–336 (1991).
56. Zenger-Hain, J., Carft, D. A. & Rizzo, W. B. New developments in fatty acid oxidation. (eds Coates, P. M. & Tanada K.) 339–407 (wiley-Liss, New York, 1992).
57. Laemmli, U. K. Cleavage of structural proteins during the assembly of the head of bacteriophage T4. *Nature* 227, 680–685 (1970).

TABLE 1

Effect of 4PBA on VLCFA (C27:0 and C26:0) levels in cultured cell lines

| Phenotype | n | Exposure (days) | Untreated | Treated | P value | Percent Correction* |
|---|---|---|---|---|---|---|
|  |  |  | (percent of total fatty acids) |  |  |  |
| Human primary fibroblasts |  |  | C24:0 |  |  |  |
| X-ALD | 6 | 1 | 2.62 ± 0.40 | 2.65 ± 0.36 | 0.988 | −1 |
| X-ALD | 4 | 6 | 2.48 ± 0.67 | 1.82 ± 0.28 | 0.122 | 81 |
| X-ALD | 10 | 12 | 2.11 ± 0.33 | 1.43 ± 0.34 | <0.001 | 155 |
| X-ALD | 7 | 16 | 2.22 ± 0.12 | 1.69 ± 0.27 | 0.001 | 96 |
| X-ALD | 4 | 22 | 2.20 ± 0.23 | 1.52 ± 0.14 | 0.006 | 128 |
| Normal | 8 |  | 1.67 ± 0.45 |  |  |  |
|  |  |  | C26:0 |  |  |  |
| X-ALD | 6 | 1 | 0.52 ± 0.15 | 0.51 ± 0.14 | 0.906 | 2 |
| X-ALD | 4 | 6 | 0.53 ± 0.13 | 0.41 ± 0.04 | 0.147 | 26 |
| X-ALD | 10 | 12 | 0.43 ± 0.08 | 0.31 ± 0.06 | 0.003 | 33 |
| X-ALD | 7 | 16 | 0.41 ± 0.06 | 0.28 ± 0.03 | <0.001 | 38 |
| X-ALD | 4 | 22 | 0.45 ± 0.05 | 0.27 ± 0.04 | 0.005 | 47 |
| Normal | 8 |  | 0.07 ± 0.02 |  |  |  |

TABLE 1-continued

Effect of 4PBA on VLCFA (C27:0 and C26:0) levels in cultured cell lines

| Phenotype | n | Exposure (days) | Untreated | Treated (percent of total fatty acids) | P value | Percent Correction* |
|---|---|---|---|---|---|---|
| Human lymphoblastoid cells | | | C24:0 | | | |
| X-ALD | 21 | 6 | 1.03 ± 0.19 | 0.65 ± 0.17 | <0.001 | 126 |
| X-ALD | 5 | 10 | 1.04 ± 0.20 | 0.54 ± 0.16 | 0.004 | 161 |
| Normal | 8 | | 0.73 ± 0.22 | | | |
| | | | C26:0 | | | |
| X-ALD | 21 | 6 | 0.21 ± 0.07 | 0.11 ± 0.05 | <0.001 | 71 |
| X-ALD | 5 | 10 | 0.26 ± 0.13 | 0.09 ± 0.05 | 0.029 | 90 |
| Normal | 8 | | 0.07 ± 0.03 | | | |
| Mouse primay fibroblasts | | | C24:0 | | | |
| X-ALD | 4 | 5 | 1.88 ± 0.08 | 1.10 ± 0.15 | 0.002 | 115 |
| X-ALD | 4 | 9 | 1.84 ± 0.10 | 0.87 ± 0.04 | 0.001 | 152 |
| Normal | 7 | | 1.20 ± 0.40 | | | |
| | | | C26:0 | | | |
| X-ALD | 4 | 5 | 0.30 ± 0.08 | 0.07 ± 0.03 | 0.005 | 92 |
| X-ALD | 4 | 9 | 0.30 ± 0.06 | 0.05 ± 0.01 | 0.002 | 100 |
| Normal | 7 | | 0.05 ± 0.02 | | | |

To assess the effect of 4PBA on VLCFA levels, we compared results obtained from treated cells with those obtained from untreated cells grown in parallel. The time of 4PBA treatment varied (Exposure). VLCFA levels were calculated as a weight percentage of the total fatty acids in the cells. Percentages are the average of mutiple assays (n) in mixed cell lines from X-ALD patients with different mutations and different phenotypes. Two of the X-ALD cell lines have detectable ALDP; all of the other cell lines have no detectable ALDP. There were no detectable differences in response to 4PBA among the various cell lines. Mouse values are for individual cell lines from different X-ALD mice with no detectable ALDP.
*The percent correction was calculated retative to the difference in the values observed in untreated X-ALD cells (0%) and the values observed in normal cells (100%). Corrections exceeding 100% indicate VLCFA levels that are lower than those observed in corresponding normal cells. P values were calculated using the two-tailed Student's t-test..

TABLE 2

The effect of 4PBA on C24:0 β-oxidation

| Cell Type | n | Untreated | Treated | P-value | Increase |
|---|---|---|---|---|---|
| X-ALD human primary fibroblasts | 15 | 0.20 ± 0.07 | 0.39 ± 0.07 | <0.0000002 | 1.95 |
| X-ALD human lymphoblastoid cells | 8 | 0.06 ± 0.01 | 0.18 ± 0.03 | <0.000003 | 2.92 |
| X-ALD mouse primary fibroblasts | 6 | 0.15 ± 0.07 | 0.28 ± 0.03 | <0.000009 | 1.87 |
| Normal human primary fibroblasts | 13 | 0.81 ± 0.14 | nd | na | na |
| Normal human lymphoblastoid cells | 7 | 0.36 ± 0.06 | nd | na | na |
| Normal mouse primary fibroblasts | 3 | 0.97 ± 0.15 | nd | na | na |

Cells were grown-in the presence or absence of 5 mM 4PBA for 6 days. C24:0 β-oxidation activities in treated cells were compared with those in untreated control cells. Values reported are mean specific activity in nmol/hr per mg protein. Equal amounts of protein (200–300 μg) from treated and untreated X-ALD cells were assayed. A 6-day exposure to 5 mM 4PBA resulted in about a twofold increase in human and mouse X-ALD fibroblasts, and about a threefold increase in the C24:0 β-oxidation in human lymphoblastoid cells. nd, not done; na, not applicable.

TABLE 3

Effect of 4PBA on peroxisome number

| Cell line | n | Untreated | Treated | P-value | Increase |
|---|---|---|---|---|---|
| Normal GM 5565 | 10 | 425 ± 144 | 961 ± 383 | <0.0008 | 2.3 |
| Normal GM 5659C | 10 | 398 ± 158 | 907 ± 270 | <0.0001 | 2.3 |
| Normal GM 5757A | 10 | 423 ± 138 | 1035 ± 338 | <0.00009 | 2.4 |
| Normal GM 5756 | 10 | 373 ± 156 | 852 ± 271 | <0.0004 | 2.3 |
| Mean | | 405 ± 24 | 939 ± 78 | <0.001 | 2.3 |
| X-ALD (A626T) | 10 | 400 ± 130 | 968 ± 349 | <0.0002 | 2.4 |
| X-ALD (R591Q) | 10 | 419 ± 198 | 1159 ± 363 | <0.00005 | 2.8 |
| X-ALD (fs E471) | 10 | 459 ± 108 | 992 ± 344 | <0.0003 | 2.2 |
| X-ALD (fs E471) | 10 | 398 ± 122 | 1089 ± 365 | <0.00005 | 2.7 |
| X-ALD (exon 7–10del) | 10 | 449 ± 138 | 1164 ± 378 | <0.00005 | 2.6 |
| Mean | | 425 ± 28 | 1074 ± 92 | <0.0002 | 2.5 |

Peroxisome numbers in human control and X-ALD primary skin fibroblasts before and after 10 day exposure to 5 mM 4PBA A 10-day exposure to 5 mM 4PBA resulted in an increase of approximately 2.4-fold in peroxisomes per cell. The X-ALD mutations are indicated in parentheses for each cell line. The fs E471 mutation was present in two independent cell lines.

What is claimed is:

1. A method of treating a patient with adrenoleukodystrophy, comprising the step of:

administering to a patient with adrenoleukodystrophy an effective amount of arginine butyrate, whereby the level of C24:0 or C26:0 fatty acids in the central nervous system of the patient is reduced.

2. The method of claim 1 further comprising the step of:

administering to the patient an effective amount of an agent which increases the expression of a peroxisomal ATP binding cassette transmembrane transporter protein in the central nervous system of the patient, said agent selected from the group consisting of: cDNA encoding ALDRP, cDNA encoding PMP70, cDNA encoding PMP69, cDNA encoding ALDP, 4-phenylbutyrate, and phenylacetate.

3. The method of claim 2 wherein the peroxisomal ATP binding cassette transmembrane transporter protein is selected from the group consisting of ALDRP, PMP70, and PMP69.

4. The method of claim 2 wherein the peroxisomal ATP binding cassette transmembrane transporter protein is ALDRP.

5. The method of claim 1 wherein the level of C24:0 or C26:0 fatty acids is reduced in the brain of the patient.

6. The method of claim 1 wherein the level of C24:0 or C26:0 fatty acids is reduced in the adrenal glands of the patient.

7. The method of claim 1 wherein arginine butyrate is administered orally.

8. A method of treating cells with a defect in adrenoleukodystrophy protein to reduce the level of C24:0 or C26:0 fatty acids in the cells, comprising the step of:

administering to the cells an effective amount of arginine butyrate, whereby the level of C24:0 or C26:0 fatty acids in the cells is reduced.

9. The method of claim 8 further comprising the step of:

administering to the cells an effective amount of an agent which increases the expression of a peroxisomal ATP binding cassette transmembrane transporter protein in the cells, said agent selected from the group consisting of: cDNA encoding ALDRP, cDNA encoding PMP70, cDNA encoding PMP69, cDNA encoding ALDP 4-phenylbutyrate, and phenylacetate.

10. The method of claim 9 wherein the peroxisomal ATP binding cassette transmembrane transporter protein is selected from the group consisting of ALDRP, PMP70, and PMP69.

11. The method of claim 10 wherein the peroxisomal ATP binding cassette transmembrane transporter protein is ALDRP.

* * * * *